United States Patent
Wang et al.

(10) Patent No.: US 11,883,554 B2
(45) Date of Patent: Jan. 30, 2024

(54) HEMOSTATIC PASTE HAVING SURFACE ENRICHED WITH HEMOSTASIS-PROMOTING AGENTS AND DEVICES FOR DELIVERY

(71) Applicant: Ethicon, Inc., Somerville, NJ (US)

(72) Inventors: Yi-Lan Wang, Somerset, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 95 days.

(21) Appl. No.: 17/229,121

(22) Filed: Apr. 13, 2021

(65) Prior Publication Data
US 2021/0228767 A1    Jul. 29, 2021

Related U.S. Application Data

(62) Division of application No. 15/807,068, filed on Nov. 8, 2017, now Pat. No. 11,007,299.

(51) Int. Cl.
*A61L 24/04* (2006.01)
*A61M 11/00* (2006.01)
(Continued)

(52) U.S. Cl.
CPC ........... *A61L 24/043* (2013.01); *A61L 24/001* (2013.01); *A61L 24/0015* (2013.01);
(Continued)

(58) Field of Classification Search
CPC ..... A61L 24/0047–0094; A61L 26/009; A61L 26/0095; A61L 26/0038; A61L 26/0033; A61L 2300/418
See application file for complete search history.

(56) References Cited

U.S. PATENT DOCUMENTS

| 4,891,359 A | 1/1990 | Saferstein et al. |
| 5,116,315 A | 5/1992 | Capozzi et al. |

(Continued)

FOREIGN PATENT DOCUMENTS

| CN | 102451499 A | 5/2012 |
| WO | 03055531 A2 | 7/2003 |

(Continued)

OTHER PUBLICATIONS

Sheikhzadeh, et al., The effect of a new syringe design on the ability of rheumatoid arthritis patients to inject a biological medication, Applied Ergonomics, 2012, pp. 368-375, vol. 43.

(Continued)

*Primary Examiner* — Todd J Scherbel
(74) *Attorney, Agent, or Firm* — David R. Crichton; Leo B. Kriksunov

(57) ABSTRACT

The present invention is directed to a hemostatic semi-solid paste material comprising a bioabsorbable carrier hemostatic material; and a supplemental hemostatic agent; wherein the paste material has an elongated form extending along a lengthwise axis with an aspect ratio of at least 3; wherein the paste is self-supporting and syringe extrudable; and wherein the supplemental hemostatic agent has a non-homogenous distribution profile across a cross-section taken across the lengthwise axis. In another aspect, the present invention relates to devices for forming and expressing the hemostatic material.

3 Claims, 8 Drawing Sheets

(51) Int. Cl.
  *A61M 5/19* (2006.01)
  *A61L 24/00* (2006.01)
  *A61L 26/00* (2006.01)

(52) U.S. Cl.
  CPC ......... *A61L 26/009* (2013.01); *A61L 26/0033* (2013.01); *A61L 26/0038* (2013.01); *A61L 26/0061* (2013.01); *A61L 26/0066* (2013.01); *A61M 5/19* (2013.01); *A61M 11/007* (2014.02); *A61L 2300/418* (2013.01); *A61L 2400/04* (2013.01); *A61L 2400/06* (2013.01)

(56) References Cited

U.S. PATENT DOCUMENTS

| | | | |
|---|---|---|---|
| 5,605,541 | A | 2/1997 | Holm |
| 5,814,022 | A | 9/1998 | Antanavich et al. |
| 6,599,627 | B2 | 7/2003 | Yeo et al. |
| 7,109,163 | B2 | 9/2006 | Pendharkar et al. |
| 7,824,601 | B1 | 11/2010 | Stankus et al. |
| 9,028,851 | B2 | 5/2015 | Wang et al. |
| 9,149,511 | B2 | 10/2015 | Wang et al. |
| 9,539,358 | B2 | 1/2017 | Wang et al. |
| 9,717,820 | B2 | 8/2017 | Wang et al. |
| 9,717,821 | B2 | 8/2017 | Schutte et al. |
| 9,833,541 | B2 | 12/2017 | McCoy et al. |
| 10,111,980 | B2 | 10/2018 | Larsen |
| 11,007,299 | B2 | 5/2021 | Wang et al. |
| 2007/0083155 | A1 | 4/2007 | Muller |
| 2007/0086958 | A1 | 4/2007 | Drake et al. |
| 2012/0021058 | A1 | 1/2012 | Goessl |
| 2012/0071884 | A1 | 3/2012 | Cooper et al. |
| 2012/0164224 | A1 | 6/2012 | Wang et al. |
| 2014/0005636 | A1 | 1/2014 | Wang |
| 2015/0125537 | A1 | 5/2015 | Goh et al. |
| 2015/0374929 | A1* | 12/2015 | Hyde .................. A61M 5/3286 604/239 |
| 2016/0074602 | A1 | 3/2016 | Wang et al. |
| 2016/0114112 | A1 | 4/2016 | Riebman et al. |

FOREIGN PATENT DOCUMENTS

| | | |
|---|---|---|
| WO | 2012039592 A1 | 3/2012 |
| WO | 2013177242 A1 | 11/2013 |
| WO | 2019092583 A1 | 5/2019 |

OTHER PUBLICATIONS

Vo, et al., The Biomechanics and Optimization of the Needle-Syringe System for Injecting Triamcinolone Acetonide into Keloids, Journal of Medical Engineering, 2016, 8 pages, Volumne 2016.

Astin A. D. "Finger Force Capability: Measurement and Prediction Using Anthropometric and Myoelectric Measures", Blacksburg, VA, USA: Faculty of the Virginia Polytechnic Institute and State University; Master of Science Thesis; 1999.

International Search Report and Written Opinion received for PCT Application No. PCT/IB2018/058681, dated Feb. 12, 2019, 15 pages.

\* cited by examiner

M　　　C

M　　　C

M　　　C

M        C

M        C

M        C

HEMOSTATIC PASTE HAVING SURFACE ENRICHED WITH HEMOSTASIS-PROMOTING AGENTS AND DEVICES FOR DELIVERY

FIELD OF THE INVENTION

The present invention is directed to flowable, semi-liquid bioresorbable hemostatic materials, particularly elongated forms of a first material coated by a second material, and to methods and devices for making and delivering such materials.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances, substantial bleeding can occur. These situations usually require specialized equipment and materials as well as personnel trained to administer appropriate aid. Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites. The control of bleeding is essential and critical in surgical procedures to minimize blood loss, to reduce post-surgical complications, and to shorten the duration of the surgery in the operating room.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized. The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

To address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin in various forms with or without a thrombin solution, collagen, chitin, chitosan, etc. To improve the hemostatic performance, scaffolds based on the above materials can be combined with biologically-derived clotting factors, such as thrombin and fibrinogen.

One of the most commonly used topical hemostatic agents is SURGICEL® Original absorbable hemostat, made from oxidized regenerated cellulose (ORC). ORC was introduced in 1960 as a safe and effective hemostatic agent for many surgical procedures. ORC fabric has a loose knit in its matrix structure and conforms rapidly to its immediate surroundings and is easier to manage than other absorbable agents because it does not stick to surgical instruments and its size can be easily trimmed. This allows the surgeon to hold the cellulose firmly in place until all bleeding stops.

Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. Many methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

SURGICEL® absorbable hemostats are used adjunctively in surgical procedures to assist in the control of capillary, venous, and small arterial hemorrhage when ligation or other conventional methods of control are impractical or ineffective. The SURGICEL® family of absorbable hemostats consists of four main product groups, with all hemostatic wound dressings commercially available from Ethicon, Inc., Somerville, N.J., a Johnson & Johnson Company:

- SURGICEL® Original hemostat is a white fabric with a pale-yellow cast, this material is strong and can be sutured or cut without fraying;
- SURGICEL® NU-KNIT® absorbable hemostat is like Original but has a denser knit and thus a higher tensile strength, this material is particularly recommended for use in trauma and transplant surgery as it can be wrapped or sutured in place to control bleeding;
- SURGICEL® FIBRILLAR™ absorbable hemostat form of the product has a layered structure that allows the surgeon to peel off and grasp with forceps any amount of material needed to achieve hemostasis at a bleeding site, may be more convenient than the knitted form for hard to reach or irregularly shaped bleeding sites and is particularly recommended for use in orthopedic/spine and neurological surgery;
- SURGICEL® SNoW™ absorbable hemostat form of the product is a structured non-woven fabric that may be more convenient than other forms for endoscopic use due to the structured, non-woven fabric and is highly adaptable and recommended in both open and minimally invasive procedures.

Protein-based hemostatic materials such as collagen and gelatin are commercially available in solid sponge, fibrillar and loose or unpacked powder form for use in surgical procedures. Mixing of the loose or unpacked powder with a fluid such as saline or thrombin may form a paste or slurry that is useful as a hemostatic composition for use in cases of diffuse bleeding, particularly from uneven surfaces or hard to reach areas, depending on mixing conditions and relative ratios of the materials.

Gelatin-based hemostats, both in solid sponge or powder form, are commercially available and are used in surgical procedures. Gelatin powder, when mixed with fluid, can form a paste or slurry that is useful as a flowable, extrudable and injectable hemostat for diffuse bleeding, particularly from uneven surfaces or hard to reach areas. The conventional slurry is prepared at the point of use by mechanical agitation and mixing of the powder and liquid to provide uniformity of the composition.

Conventional slurries are prepared at the point of use by mechanical agitation and mixing of loose powder and liquid to provide uniformity of the composition. Mixing of the powder and fluid may be conducted in a container, such as a beaker. Alternately, one syringe can be preloaded with gelatin, and a second syringe with liquid. When it is time to make a paste, syringes are connected via a luer lock and the liquid and gelatin can be passed repeatedly back and forth between syringes so that a homogeneous paste may be formed.

SURGIFLO® Hemostatic Matrix Kit, available from Ethicon, Inc., Somerville, N.J., contains SURGIFLO® Hemostatic Matrix with thrombin and provides a matrix for platelet adherence, accelerating the formation of the platelet plug and aids in fibrin clot formation. It contains EVITHROM® Thrombin, Topical (Human), Lyophilized Powder for Solution. Absorbable Haemostatic Gelatin Flowable Matrix—with/without Thrombin a sterile, absorbable gelatin paste intended for haemostatic use by applying to a bleeding surface. The gelatin paste is supplied in a pre-filled syringe to be homogenously mixed with 2 ml of additional liquid (sterile saline solution or thrombin).

U.S. Patent Application publication No. 2016/0074602A1 titled Methods and Devices for Co-Delivery of Liquid and Powdered Hemostats and Sealants discloses an integrated delivery device operable with one hand and for co-delivery of a liquid medicant and a powder medicant onto a tissue or wound comprising at least two integrated medicant expression subunits of a) liquid medicant expression subunit and b) powder medicant expression subunit, each expression subunit having an actuator for the medicant contained therein, the actuators are positioned in close proximity to each other at a proximate end of said expression subunits, and delivery cannulas for each of said expression subunits that positioned in close proximity to each other at a distal end of said expression subunits.

U.S. Pat. No. 5,605,541 titled Fibrin sealant applicator discloses a method for applying two components of a fibrin sealant which method comprises a simultaneous discharge from a spray head of a fibrin sealant applicator of a gas vehicle through a center hole in an exit end and centrally located within said spray head; a first fibrin sealant forming component through a first annular aperture concentric with and spaced radially outward from said center hole; and a second fibrin sealant forming component through a second annular aperture concentric with and spaced radially outward from said center hole and said first annular aperture, whereby a uniform efficient application of the components to form a uniform fibrin sealant is provided.

U.S. Pat. No. 7,824,601 titled Process of making a tubular implantable medical device discloses a method of fabricating a tubular implantable medical device comprising: electrospinning a polymer fluid through a coaxial nozzle to form fibers of the polymer, the coaxial nozzle having an outer passageway containing the polymer fluid and an inner passageway containing biodegradable polymer particles, wherein at least some of the particles are encapsulated within the formed fibers upon exiting the nozzle and forming the fibers; depositing the fibers over a tubular support to form a tubular fibrous layer; and forming a stent from the tubular fibrous layer.

U.S. Pat. No. 6,599,627 titled Microencapsulation of drugs by solvent exchange discloses a method for preparing an encapsulated composition, comprising: providing an aqueous solution composed of water and a core substance dissolved therein; providing a polymer solution composed of a water-miscible solvent and a water-insoluble polymer dissolved therein; forming a droplet of the aqueous solution containing the core substance using at least one syringe, single nozzle, coaxial nozzle, or microdispenser device; and admixing the droplet of aqueous solution with at least a portion of the polymer solution under conditions permitting the water-soluble polymer to deposit as at least one layer on the core substance, thereby affording the encapsulated composition.

U.S. Patent Application publication No. 2007/0083155A1 titled Multi-lumen injection apparatus discloses an injection apparatus for delivering a plurality of medicaments, the apparatus comprising: a hollow inner needle defining a first lumen fluidically couplable to a first medicament reservoir and a first fluid delivery actuator; a hollow outer needle having a distal end that at least partially surrounds the inner needle, the outer needle defining a second lumen fluidically couplable to a second medicament reservoir and a second fluid delivery actuator; whereby the injection apparatus can be used to penetrate tissue and independently deliver at least two separate medicaments from said first and second medicament reservoirs.

U.S. Pat. No. 5,814,022 titled Method and apparatus for applying tissue sealant discloses a dispenser comprising: a plurality of separate parallel cylindrical compartments arranged concentrically, each of said cylindrical compartments having an outlet port at one end, a number of plungers equal to said plurality of cylindrical compartments, and a manifold having separate means for transporting fluid through the manifold from the outlet port of each cylindrical compartment to a common location on the surface of the manifold opposite said outlet ports.

U.S. Patent Application publication No. 2016/0114112A1 titled Distance Indicators for Medicinal Spray Devices discloses a spray applicator for delivery of a medicant onto a tissue surface comprising a container containing a medicant and positioned at a proximal end of the spray applicator; a spray tip positioned at a distal end of the spray applicator; a cannula connecting the container with the spray tip; a dispensing mechanism at a proximal end of the applicator to express the medicant from the container through the cannula and the spray tip toward the tissue surface; a distance indicator that is deployable between the spray tip and the tissue and provides visual or tactile observation indicia of a distance between the spray tip and the tissue but does not prevent positioning of the spray tip closer to the tissue than the observed distance; and an optional pressurized gas source in fluid communication with the spray tip through the cannula providing gas in the vicinity of the spray tip or within the spray tip.

SUMMARY OF THE INVENTION

The present invention is directed to a hemostatic semi-solid paste material comprising: a bioabsorbable carrier hemostatic material and a supplemental hemostatic agent; wherein the paste material has an elongated form extending along a lengthwise axis with an aspect ratio of at least 3; wherein the paste is self-supporting and syringe extrudable; and wherein the supplemental hemostatic agent has a non-homogenous distribution profile across a cross-section taken across the lengthwise axis. The elongated form is enriched with supplemental hemostatic agent that is present exclusively or primarily on an outside surface of the elongated form or in an outside layer of the elongated form.

The carrier hemostatic material can be gelatin or collagen. The supplemental hemostatic agent can be oxidized cellulosic material, hemostatically active enzyme, platelet aggregating peptide, hemostatic solvent extract of a natural material, or combinations thereof. The supplemental hemostatic agent can comprise oxidized regenerated cellulose in a form of a powder or thrombin or thrombin mixed with gelatin.

The present invention further relates to a delivery device for forming and expressing the hemostatic paste material comprising: a first syringe containing the carrier material; a second syringe containing at least the supplemental hemostatic agent; with first and second syringes forming an integrated unit and connected to a coaxial expression tip configured for simultaneous expression of the carrier material and the supplemental hemostatic agent; wherein the coaxial expression tip comprises an external tube and an internal tube positioned within said external tube, with a gap between the external tube and an internal tube.

The present invention further relates to a method of treating a wound comprising the step of applying the hemostatic paste material onto and/or into the wound of a patient.

DETAILED DESCRIPTION

Figure 1A:
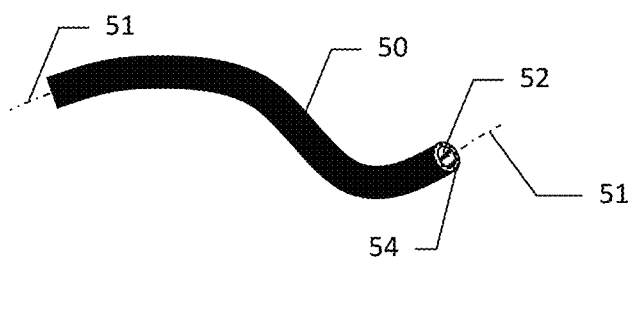
FIGS. 1a, 1b, 1c show schematic perspective and cross-sectional views of embodiments of the present invention.

Hemostatic paste (such as gelatin particles mixed with and or dispersed in water or aqueous solutions) is frequently homogeneously mixed with an additional or supplemental hemostatic agent (such as thrombin) that activates, initiates, accelerates or otherwise enhances the efficacy of the hemostatic cascade once in contact with blood plasma prior to administration onto a wound. The additional hemostatic agent, which is consequently largely contained within the bulk of the paste, is not exposed to the bleeding wound surface at the earliest possible time. The additional hemostatic agent which is in the bulk of the paste thus may not be able to immediately contribute to hemostatic biologic processes on bleeding surfaces, potentially adding to unnecessary costs and need to absorb the agent which was not timely available for hemostasis.

According to an embodiment of the present invention, an absorbable carrier hemostatic composition, preferably a flowable viscous semi-liquid fluid or paste, has an elongated rod-like or "noodle-like" shape with a surface enriched with a hemostasis promoting agent. In one embodiment, the flowable viscous semi-liquid fluid or paste having elongated rod-like shape comprises a scaffold or matrix or carrier, onto which a hemostatic agent or a layer of absorbable material enriched with a hemostasis promoting agent is deposited.

The additional or supplemental hemostatic agent can be thrombin or thrombin equivalent or any other hemostasis-promoting, and/or clotting promoting, and/or platelet aggregation promoting active material, such as enzyme, protein, peptide, molecule, natural material, modified natural material such as oxidized cellulose (OC) or oxidized regenerated cellulose (ORC), solvent extract, or particle, or particle aggregates.

U.S. Pat. No. 9,539,358 by Yi-Lan Wang, Guanghui Zhang "Oxidized regenerated cellulose hemostatic powders and methods of making", which is incorporated by reference herein in its entirety, discloses various ORC coarse and fine fiber particles as well as particle aggregates that can be utilized as supplemental hemostatic agent in practicing the present invention.

U.S. Pat. Nos. 9,717,820; 9,149,511 by Yi-Lan Wang, Guanghui Zhang "Procoagulant peptides and their derivatives and uses therefor", incorporated by reference herein, discloses hemostatically active peptides that can be utilized as supplemental hemostatic agent in practicing the present invention.

U.S. Pat. No. 9,028,851 by Yi-Lan Wang et al. "Hemostatic materials and devices with galvanic particulates" incorporated by reference herein, discloses hemostatically active galvanic particulates that can be utilized as supplemental hemostatic agent in practicing the present invention.

U.S. Patent Application Publication No. 20120164224 by Yi-Lan Wang et al. "Hemostatic Preparation Containing an Extract of Golden Moss" incorporated by reference herein, discloses hemostatically active Extract of Golden Moss plant that can be utilized as supplemental hemostatic agent in practicing the present invention.

Figure 1B:
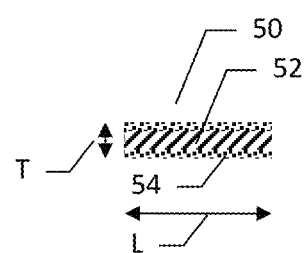

Referring now to FIG. 1, an embodiment of the present invention shown. FIG. 1a shows a schematic perspective view of elongated hemostatic paste shape 50 having an inside portion 52 comprising absorbable carrier hemostatic material not enriched with additional hemostasis promoting agents, or enriched to a lesser extent with additional hemostasis promoting agents, said inside portion 52 surrounded by an outside or surface portion or layer 54 which is enriched with hemostasis promoting agents than inside portion 52. As shown, elongated shape 50 running along a lengthwise axis 51 and can be straight or bent and undulating in a wavy form along axis 51. FIG. 1b shows a schematic cross-sectional view of hemostatic paste shape 50 with inside portion 52 and enriched surface layer 54 shown. According to an embodiment of the present invention, the concentration of hemostasis promoting agents is higher in the surface portion 54 relative to inside portion 52.

Elongated hemostatic paste shape 50 can have any cross-sectional shape depending on the expression tip, such as elliptical, square, rectangular, triangular, etc., most typically circular cross-section. The diameter can be any convenient diameter, such as ranging from 0.25 mm to 15 mm, more preferably 0.5 mm to 5 mm, such as 1, 2, 3, 5, 7 mm diameter. The length of hemostatic paste shape 50 having elongated rod-like or "noodle-like" shape can be any convenient length, such as from 2 mm to 300 mm, such as 5, 10, 20, 30, 50, 100 mm. Surface layer 54 encompasses a range from the agent being only adhering to the surface to enriching surface layer 54 (zero depth penetration) to a depth of from 0 to 25, 50, 100, 200, 300, 500, 1000, 2000 microns, such as 50, 100 or 300 microns. Alternatively, surface layer 54 comprises from 0.1% to 25% of overall thickness or diameter of hemostatic paste shape 50, such as 1, 5, 10% of overall thickness or diameter.

As shown in FIG. 1b, lengthwise dimension L of elongated hemostatic paste shape 50 is much larger than largest transverse or cross-sectional dimension T, defining aspect ratio A as a ratio of L to T, or A=L/T. Aspect ratio is preferably at least 3, more preferably at least 5, such as 5, 10, 15, 20, 50, 100 or higher. For elongated hemostatic paste shape 50 having diameter of 2 mm and length of 30 mm, A=15.

Figure 1C:
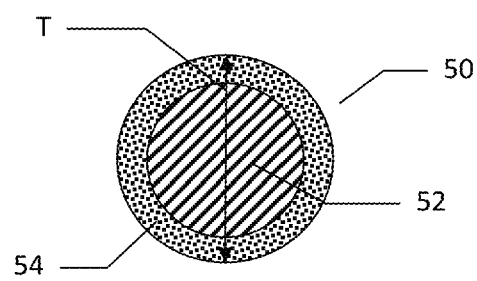

As shown in FIG. 1c, showing cross-sectional view of elongated hemostatic paste shape 50 with cross-section taken across the lengthwise axis 51, the supplemental hemostatic agent has a non-homogenous distribution profile across a cross-section taken across the lengthwise axis 51, with higher concentration within outside or surface portion or layer 54 close to the surface of elongated form 50, and lower concentration or no supplemental hemostatic agent in the inside portion 52.

Advantageously, it is postulated that for the inventive test article, comprising a given quantity Q of hemostasis-promoting agent disposed on or in surface layer 54, the hemostatic performance is better than performance of a comparative test article, comprising the same given quantity Q of hemostasis-promoting agent homogeneously mixed into elongated hemostatic paste shape 50.

Further, it is postulated that for the inventive test article, comprising a given quantity Q of hemostasis-promoting agent disposed on or in surface layer 54, the hemostatic performance is equal to or better than performance of a comparative test article, comprising larger quantity of hemostasis-promoting agent homogeneously mixed into elongated hemostatic paste shape 50, such as quantity equal to 1.5 Q, 2 Q, 3 Q, 5 Q, 10 Q, or similar.

Advantageously, according to the present invention, the hemostatic performance is either improved when the same quantity of hemostatic agent is disposed on or in surface layer 54, comparative to the hemostasis-promoting agent homogeneously mixed into elongated hemostatic paste shape 50. Alternatively, or additionally, the same hemostatic performance can be achieved with a smaller quantity of hemostatic agent disposed on or in surface layer 54, comparative to the hemostasis-promoting agent homogeneously mixed into elongated hemostatic paste shape 50.

According to the present invention, presence of hemostasis promoting agents disposed on or in surface layer 54 provides for faster access of the agents to the bleeding site and/or tissue in the first several seconds or minutes when hemostasis is established; on the contrary the hemostasis promoting agents that are buried deeply inside elongated hemostatic paste shape 50 have lesser availability to affect hemostasis during the critical first several seconds or minutes when hemostasis is sought.

Example 1. Gelatin Paste with ORC Coating Testing for Clotting with Porcine Blood A gelatin paste commercially available as SURGIFLO® Hemostatic Matrix, available from Ethicon, Inc., Somerville, N.J., (which comprises sterile, absorbable cross-linked gelatin paste intended for hemostatic use by applying to a bleeding surface) was prepared according to the Instructions for use by mixing with normal saline. The gelatin paste was then formed into elongated rod-like shape by expression from a syringe and coated on its surface with 10% by weight of oxidized regenerated cellulose (ORC) fine fibers. As a comparative test, the gelatin paste was also homogeneously mixed with 10% by weight of ORC fine fibers and then then formed into elongated rod-like shapes by expression from a syringe.

ORC coarse and fine fiber can be obtained as follows. A reference is made to the U.S. Pat. No. 9,539,358 Oxidized regenerated cellulose hemostatic powders and methods of making, which is incorporated by reference herein in its entirety for all purposes.

One method of obtaining ORC coarse and fine fiber directly from cellulosic materials, such as ORC fabric or non-woven products such as these discussed above is as follows.

Briefly, manufacturing process starts with ORC material, such as SURGICEL® Original absorbable hemostat, as which is cut into 1- to 2-inch wide sections before the material is fed into a blade that cuts the fabric into smaller pieces. The cut ORC fabric pieces are then ground into intermediate ORC fine fibers by two consecutive milling processes (hammer milling and air classifier milling). In an alternative embodiment, the cut ORC fabric pieces are converted directly into intermediate fine fibers in a ball mill.

More specifically, one process for manufacturing the ORC fine fiber comprises the steps of: a) slitting and cutting of cellulosic source material; b) milling the resulting material from step a); c) a second milling step in an air classifier.

Slitting and cutting can preferably be performed to slit and cut fabric into appropriate size pieces that are between approximately 1 inch by 3 inches or 2 inches by 3 inches, though smaller pieces can also be used. The main operations performed for slitting and cutting are to unwind a roll of fabric, slit the fabric into strips, cut the strips to size and deliver the cut pieces into the first milling step. Many cutting and slitting machines are known and commercially available, such as AZCO Model FTW-1000 available from AZCO. In the first milling step, processed pieces of cellulosic fabric are converted from an intermediate coarse fiber produced in the slitting and cutting step to a material having a D90 value of less than 452 μm and D50 value of less than 218 μm, while having minimal impact on the color index and water-soluble content of the material. Many machines for milling are commercially available, such as Models DASO6 and WJ-RS-D6A manufactured by Fitzpatrick, which are hammer mill type milling machines, equipped with a 497 micron round screen and a set of blades that breaks down the fabric until it passes through the screen to produce intermediate coarse cellulosic fiber.

In an exemplary processing run, mill speed can be about 7000 RPM; processing temperature at less than 80° C.; screen size between 1534 and 9004; number of blades as 8 (2 impellers each); blade type as a 225 knife, impact type blades; blade orientation set as "impact".

At this stage in the preferred process, the size of the intermediate coarse fiber produced in the first milling step is further reduced to a D90 value of less than 177 μm and a D50 value of less than 95 μm while keeping a minimal impact on the color index and water-soluble content of the material. Many machines are available for second milling step, such as an Air Classifier/F10 Quadro Fine Grind from Quadro.

Intermediate coarse fiber from the first milling step can be fed at a controlled rate into the second mill and passed through two milling chambers that are separated by a milling screen. The material can be pulled through the milling chamber by an air blower. The intermediate coarse fiber can be processed through the air classifier equipment three times to obtain the desired size. At the end of the second milling step, the intermediate fine fiber can be collected.

In an exemplary processing run, a Quadro Air Classifier F10 can be used in the second milling step with a milling speed of 8400 rpm, blower speed of 1800 rpm, 0.0018" round hole screen and 3 passes. ORC intermediate fine fiber can be also produced in one step by ball milling instead of the two steps milling steps as described above. In an alternative ball milling embodiment, 50 g of pre-cut ORC fabric (2"×2") is ball milled with 12 high-density Zirconia (zirconium dioxide ZrO2, 20 mm in diameter; Glen Mills Inc., Clifton, N.J., USA) by placing the balls and the samples in a 500-mL grinding jar. The jar is clamped into the latching brackets and then counterbalanced on the planetary ball mill PM100; Retsch, Inc., Newtown, Pa., USA). The milling is then performed bi-directionally at 450 rpm for 20 minutes.

Figures 2A, 2B, 2C:
FIGS. 2a, 2b, 2c show comparative results of in vitro testing.

A quantity of 10% w/w of ORC fine powder was used to enrich surface to make surface enriched (inventive embodiment) and homogeneously mixed (comparative test) paste was then added to a vial containing 4 ml of porcine blood. FIG. 2 shows a photograph of three vials containing porcine blood after 4 minutes. FIG. 2a shows control (porcine blood, no additions). FIG. 2b shows comparative test whereby to the vial with porcine blood was added the gelatin paste homogeneously mixed with 10% by weight of ORC fine fibers. FIG. 2c shows the inventive embodiment whereby to the vial with porcine blood was added the gelatin paste enriched only on its surface with 10% by weight of ORC fine fibers. As can be seen from FIG. 2, pure blood shows no clotting, gelatin paste homogeneously mixed with ORC shows minor clotting of blood, while the inventive embodiment of gelatin paste enriched only on its surface with the same amount of ORC fine fibers shows substantial/complete clotting.

Not shown in FIG. 2 is another control test whereby gelatin paste not enriched by ORC at all was also added to the vial with porcine blood. No clotting was observed.

Thus, the inventive paste enriched on its surface with hemostatic agents demonstrates an advantage over homogeneously admixed agent in the same quantity and over paste having no added agent.

Figure 3A:
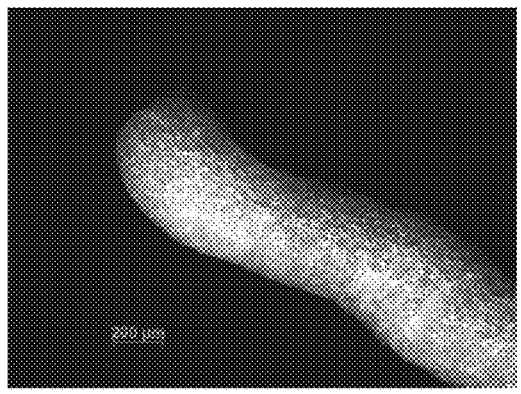
FIGS. 3a, 3b show photo images corresponding to prior art.
Figure 3B:
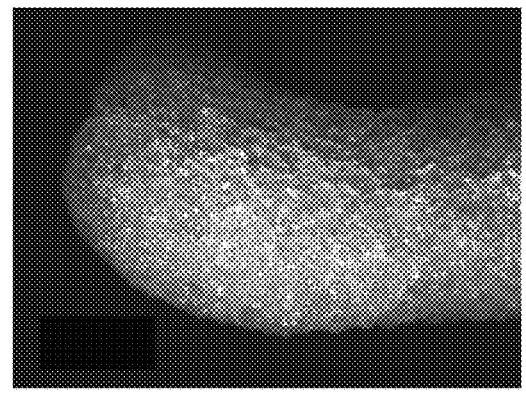

Example 2. Preparation of Gelatin Paste and Gelatin Paste with Homogenously Admixed Agents for Testing of In Vitro Clotting with Human Blood Surgiflo™ gelatin was thoroughly mixed with 2 ml saline (0.9% NaCl Irrigation USP). FIGS. 3a, 3b show photos at different magnifications of the resulted expressed elongated hemostatic paste shapes, not coated with any agents and not mixed with any agents.

Figure 4A:
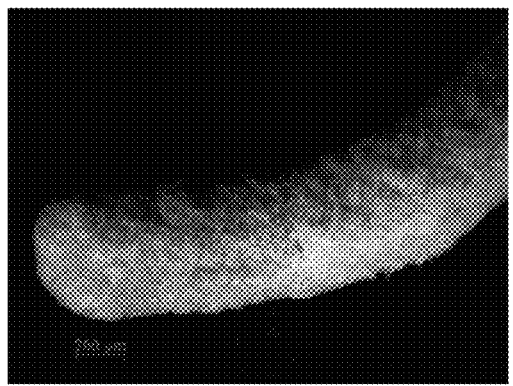
FIGS. 4a, 4b show photo images of embodiments of the present invention.
Figure 4B:
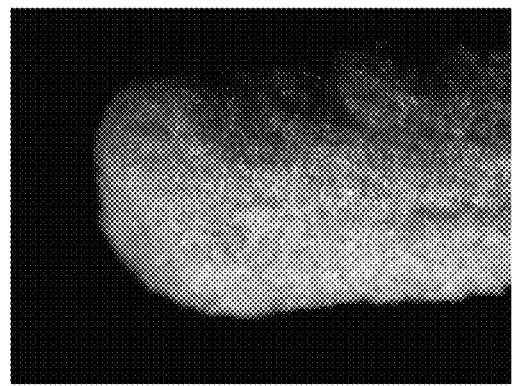
Figure 7A:
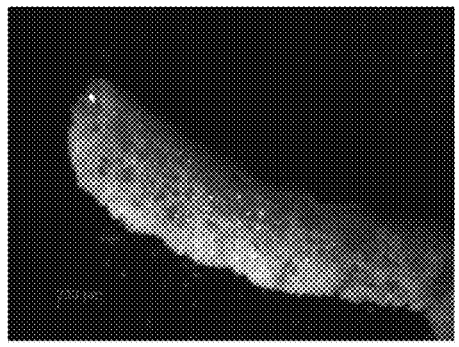
FIGS. 7a, 7b show photo images of embodiments of the present invention.
Figure 7B:
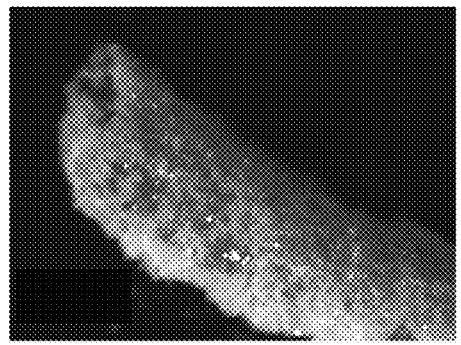

The scale is shown in FIGS. 3a, 4a, 7a by a 200-micron bar marker. FIGS. 3b, 4b, 7b are magnified 1.6 times vs. photos in FIGS. 3a, 4a, 7a.

To prepare comparative testing samples, Surgiflo™ gelatin was thoroughly mixed with 2 ml saline (0.9% NaCl Irrigation USP) and further homogenously mixed with hemostatic agents, including ORC fine powders, ORC coarse fibers, thrombin, and then expressed as elongated hemostatic paste shapes having homogenously admixed one of the above agents uniformly distributed through the paste.

Example 3. Preparation of Gelatin Paste Surface Coated with ORC Fine Fibers and Testing of In Vitro Clotting with Human Blood Elongated hemostatic paste shapes prepared as described in Example 2 were coated on the surface by ORC fine fibers powder characterized by d50: 78 μm and d90: 157 μm.

FIGS. 4a, 4b show photos at different magnifications of the resulted expressed elongated hemostatic paste shapes.

Elongated hemostatic paste shapes were then added (about 1 g, see Table 1) to vials containing sodium citrate treated (3.2%) human blood (4 ml) with no mixing.

Figure 5A:
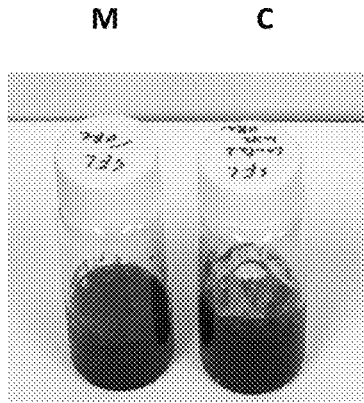
FIGS. 5a, 5b, 5c show comparative results of in vitro testing.
Figure 5B:
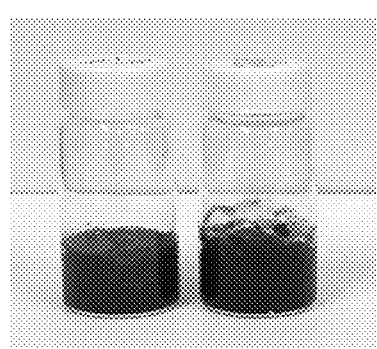

FIGS. 5a and 5b show photographs of vials in different views immediately after adding to the vials comparative test article (elongated hemostatic paste shapes comprising gelatin homogenously mixed with fine ORC fibers as described in Example 2), indicated with letter "M"; and the inventive test article (elongated hemostatic paste shapes comprising gelatin surface coated with fine ORC fibers), indicated with letter "C".

Figure 5C:
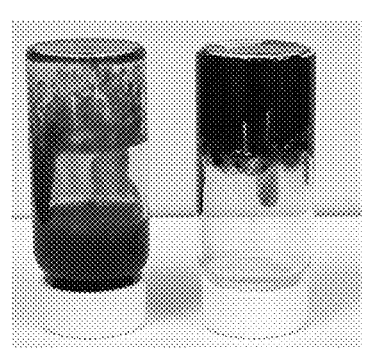

After 3 minutes, the vials were turned over with the bottoms of the vials facing upwardly, to characterize clotting. FIG. 5c shows photographs of vials after turning the vials over. The inventive test article indicated with letter "C" shows all blood substantially clotted and remaining in the upward portion of the turned over vial, indicating strong clotting performance. The comparative test article indicated with letter "M" shows all blood substantially migrated down and not remaining in the upward portion of the turned over vial, indicating very poor clotting performance. Thus, the inventive test article of elongated hemostatic paste shapes comprising gelatin surface coated with fine ORC fibers performed much better than test articles with homogenously admixed agent.

Table 1 shows the amounts of gelatin and added ORC coating used, whereby on average about 32% of ORC coating by weight was added in 4 testing replicates.

TABLE 1

Amounts of gelatin and added ORC coating used

| Sample No. | Weight of gelatin, g | Weight of gelatin coated with ORC, g | Amount of ORC added, g |
|---|---|---|---|
| A-1 | 0.75 | 0.990 | 0.240 |
| A-2 | 0.78 | 0.928 | 0.148 |
| A-3 | 0.81 | 1.108 | 0.298 |
| A-4 | 0.8 | 1.121 | 0.321 |
| AVERAGE | 0.785 | 1.037 | 0.252 |
| Coating % | 32.07% | | |

Table 2 shows experimental measurements to quantify clotting.

TABLE 2

Experimental measurements to quantify clotting, 3 replicates

| | TEST 1 | | TEST 2 | | TEST 3 | |
|---|---|---|---|---|---|---|
| | Gelatin mixed with ORC | Gelatin coated with ORC | Gelatin mixed with ORC | Gelatin coated with ORC | Gelatin mixed with ORC | Gelatin coated with ORC |
| vial + cap weight, g | 14.509 | 14.625 | 14.034 | 14.521 | 14.921 | 14.263 |
| Paste weight, g | 1.148 | 1.088 | 1.003 | 1.006 | 1.242 | 1.212 |
| Blood weight, g | 3.938 | 4.034 | 4.024 | 3.983 | 3.832 | 3.992 |
| Paste + blood weight, g | 5.086 | 5.122 | 5.027 | 4.989 | 5.074 | 5.204 |
| total vial, cap, paste, blood weight, g | 19.595 | 19.747 | 19.061 | 19.51 | 19.995 | 19.467 |
| weight after turning over | 15.883 | 19.509 | 15.002 | 19.157 | 15.532 | 18.834 |

TABLE 2-continued

Experimental measurements to quantify clotting, 3 replicates

|  | TEST 1 | | TEST 2 | | TEST 3 | |
| --- | --- | --- | --- | --- | --- | --- |
|  | Gelatin mixed with ORC | Gelatin coated with ORC | Gelatin mixed with ORC | Gelatin coated with ORC | Gelatin mixed with ORC | Gelatin coated with ORC |
| and draining any flowable fraction, g |  |  |  |  |  |  |
| flowable/moveable fraction, g | 3.712 | 0.238 | 4.059 | 0.353 | 4.463 | 0.633 |
| remaining non-flowable clotted fraction, % | 27.02 | 95.35 | 19.26 | 92.92 | 12.04 | 87.84 |

As shown in Table 2, measurements performed during the testing indicated that in the comparative test articles (gelatin homogenously mixed with ORC), remaining non-flowable clotted fraction was low, such as only 27, 19, 12% of the original content of the vial. For the inventive test article (gelatin on the surface coated with ORC), remaining non-flowable clotted fraction was very high, such as 95, 93, 88% of the original content of the vial, indicating much better clotting performance of the inventive surface coated test articles.

Example 4. Preparation of Gelatin Paste Coated with Coarse ORC Fibers

Elongated hemostatic paste shapes prepared as described in Example 2 were coated on the surface by coarse ORC fibers powder characterized by d50: 157 μm, d90: 296 μm. ORC coarse fibers were dyed with 1.4% (w/v) of Methylene blue in 95% ethanol (Sigma-Aldrich) to improve visibility of the coating.

Figure 6A:
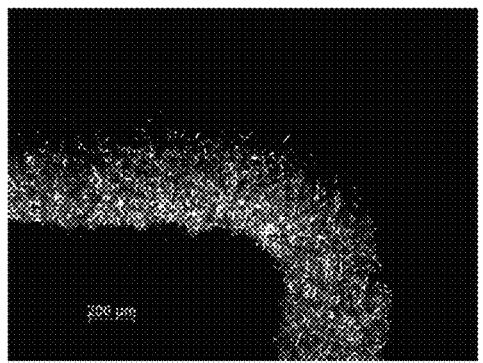
FIGS. 6a, 6b show photo images of embodiments of the present invention.
Figure 6B:
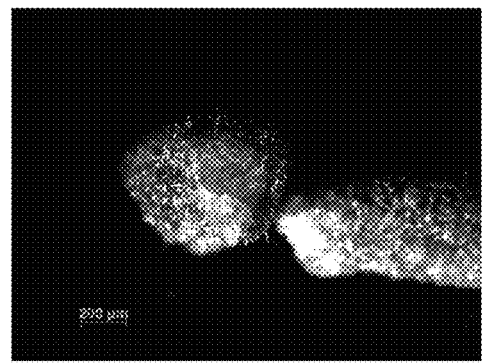

FIGS. 6a, 6b show two photos at different magnifications of the resulted expressed elongated hemostatic paste shapes.

Example 5. Preparation of Gelatin Paste Coated with Thrombin and Testing of In Vitro Clotting with Human Blood Elongated hemostatic paste shapes prepared as described in Example 2 were coated on the surface with finely ground thrombin powder. Thrombin was obtained from the Surgiflo® kit and then milled to form a powder. FIGS. 7a, 7b show two photos at different magnifications of the resulted expressed elongated hemostatic paste shapes coated with milled thrombin powder.

Figure 8A:
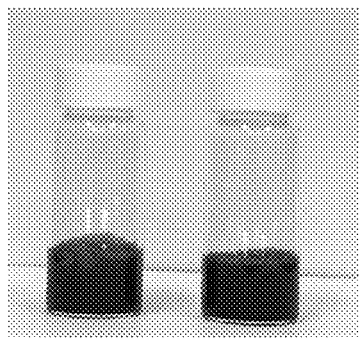
FIGS. 8a, 8b, 8c show comparative results of in vitro testing.
Figure 8B:
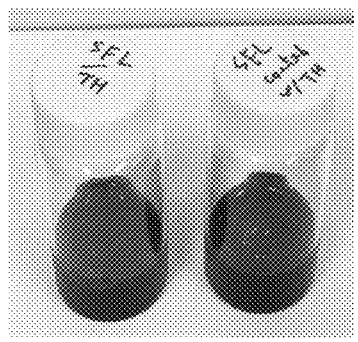

FIGS. 8a and 8b show photographs of vials in different views immediately after adding to the vials a comparative test article (elongated hemostatic paste shapes comprising gelatin homogenously mixed with thrombin), indicated with letter "M"; and the inventive test article (elongated hemostatic paste shapes comprising gelatin surface coated with milled thrombin powder), indicated with letter "C".

Figure 8C:
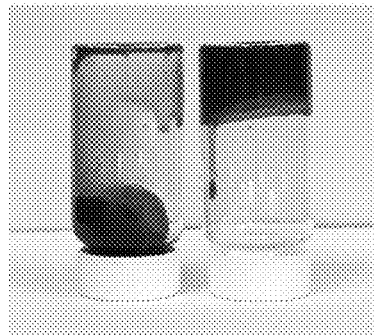

After 3 minutes, the vials were turned over with the bottoms of the vials facing upwardly, to characterize clotting. FIG. 8c shows photographs of vials after turning the vials over. The inventive test article indicated with letter "C" shows all blood substantially clotted and remaining in the upward portion of the turned over vial, indicating strong clotting performance. The comparative test article indicated with letter "M" shows blood, while somewhat clotted, substantially migrated down and not remaining in the upward portion of the turned over vial, indicating much weaker clotting performance vs. the coated test article of the present invention. Thus, the inventive test article of elongated hemostatic paste shapes comprising gelatin surface coated with thrombin performed substantially better than test articles with homogenously admixed thrombin as hemostatic agent.

Table 3 shows the amounts of gelatin and added thrombin powder coating used, whereby on average about 36% of thrombin coating by weight was added.

TABLE 3

Amounts of gelatin and added thrombin coating used, 4 replicates

| Sample No. | Weight of gelatin, g | Weight of gelatin coated with thrombin, g | Amount of thrombin added, g |
| --- | --- | --- | --- |
| B-1 | 0.104 | 0.136 | 0.032 |
| B-2 | 0.121 | 0.173 | 0.052 |
| B-3 | 0.101 | 0.145 | 0.044 |
| B-4 | 0.127 | 0.165 | 0.038 |
| AVE | 0.113 | 0.155 | 0.042 |
| Coating % | 36.64% | | |

Table 4 shows experimental measurements to quantify clotting in thrombin testing. Note that if clot formed but has moved from the vial upon turning vial over, it was considered a weak clot and a part of drained flowable/moveable fraction.

TABLE 4

Experimental measurements to quantify clotting, 3 replicates

|  | TEST 1 | | TEST 2 | | TEST 3 | |
| --- | --- | --- | --- | --- | --- | --- |
|  | Gelatin mixed with Thrombin | Gelatin coated with Thrombin | Gelatin mixed with Thrombin | Gelatin coated with Thrombin | Gelatin mixed with Thrombin | Gelatin coated with Thrombin |
| vial + cap weight, g | 14.616 | 14.556 | 14.503 | 14.764 | 14.892 | 14.931 |
| Paste weight, g | 0.553 | 0.552 | 0.503 | 0.502 | 0.631 | 0.611 |
| Blood weight, g | 4.083 | 3.997 | 4.001 | 3.83 | 3.972 | 3.892 |
| Paste + blood weight, g | 4.636 | 4.549 | 4.504 | 4.332 | 4.603 | 4.503 |
| total vial, cap, paste, blood weight, g | 19.252 | 19.105 | 19.007 | 19.096 | 19.495 | 19.434 |

TABLE 4-continued

Experimental measurements to quantify clotting, 3 replicates

| | TEST 1 | | TEST 2 | | TEST 3 | |
|---|---|---|---|---|---|---|
| | Gelatin mixed with Thrombin | Gelatin coated with Thrombin | Gelatin mixed with Thrombin | Gelatin coated with Thrombin | Gelatin mixed with Thrombin | Gelatin coated with Thrombin |
| weight after turning over and draining any flowable/moveable fraction, g | 15.082 | 19.009 | 15.104 | 18.789 | 15.323 | 19.198 |
| flowable/moveable fraction, g | 4.17 | 0.096 | 3.903 | 0.307 | 4.172 | 0.236 |
| remaining non-flowable clotted fraction, % | 10.05 | 97.89 | 13.34 | 92.91 | 9.36 | 94.75 |

As shown in Table 4, measurements performed during the testing indicated that in the comparative test articles (gelatin paste homogenously mixed with thrombin), remaining non-flowable clotted fraction was low, such as only 10, 13, 9% of the original content of the vial. For the inventive test article (gelatin paste coated with thrombin), remaining non-flowable clotted fraction was very high, such as 98, 93, 95% of the original content of the vial, indicating much better clotting performance of the inventive coated test articles.

Delivery Devices

Paste Coated by Enriched Paste

According to embodiments of the present invention, there are provided delivery devices for making and expressing elongated hemostatic paste shapes 50 having outside or surface portion or layer 54 which is enriched with hemostasis promoting agents than inside portion 52.

Figure 9:
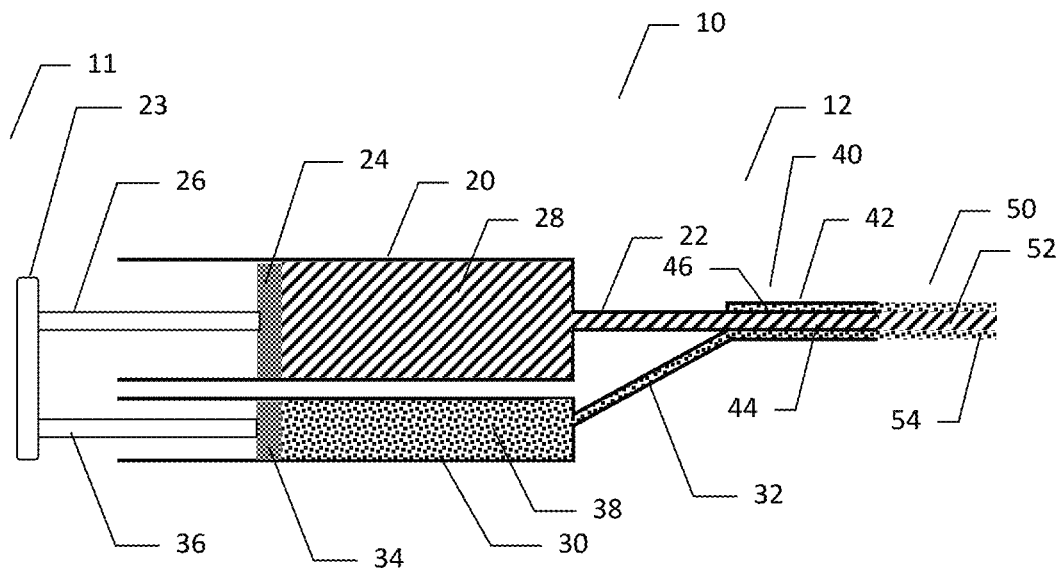
FIG. 9 shows a schematic cross-sectional view of an embodiment of the present invention.

Referring now to FIG. 9, an embodiment of the present invention shown in a schematic cross-sectional view. Delivery device 10 comprises a dual barrel syringe comprising a first barrel hollow body 20 and a second barrel hollow body 30, with pistons 24 and 34 slidably disposed inside first body 20 and second body 30. Pistons 24 and 34 are simultaneously actuated by plungers 26 and 36 terminating in a unified handle 23 at a proximal end 11. First body 20 and second body 30 at a distal end 12 have expression cannulas 22 and 32 through which a first flowable material 28 contained inside first body 20 and a second flowable material 38 contained inside second body 30 can be simultaneously co-expressed onto a wound through a coaxial expression nozzle or expression tip 40, which is open at a distal end 12. Coaxial expression tip 40 comprises internal tube 44 for expression of first material 28, with tube 44 located inside and within an external tube 42 serving for expression of second material 38. As shown, tube 42 surrounds tube 44 with a gap 46 between tubes allowing second material 38 to move alongside and outside of tube 44. Both materials 28 and 38 exit coaxial expression tip 40 jointly as elongated rod-like or noodle-like shape, with second material 38 attaching onto outside of first material 28, forming elongated hemostatic paste shape 50 having an inside portion 52 comprising first material 28 and surrounded by an outside or surface portion or layer 54 comprising second material 38.

The size or volume or diameters of first barrel hollow body 20 and second barrel hollow body 30 can be the same, or different as shown in FIG. 9, whereby second barrel hollow body 30 can be smaller diameter as shown, same diameter (not shown), or larger diameter (not shown).

In one embodiment, first material 28 comprises bioabsorbable carrier hemostatic material that comprises gelatin, collagen, or similar viscous flowable paste suitable for expression onto/into wounds. Second material 38 comprises a supplemental hemostatic agent or hemostasis promoting agent, such as thrombin powder, thrombin solution, ORC, OC, or similar, or mixtures thereof, optionally homogenously mixed with a thickener or filler or carrier hemostatic material, such as gelatin or collagen or similar viscous flowable paste, forming second material 38 that is enriched with additional hemostasis promoting agent. Preferably, both materials 28 and 38 have similar viscosity, such as viscosity within 0%-30% difference, such as 5, 10, 20% viscosity difference or less.

In operation, in one embodiment, gelatin paste is filled as first material 28 into first body 20 and gelatin paste (as a thickener or filler) premixed with thrombin is filled into second body 30 as second material 38. Depressing handle 23 towards distal end 12 is advancing plungers 26 and 36 and pistons 24 and 34 towards distal end 12 inside bodies 20, 30, thus forming at the exit of coaxial expression tip 40 elongated hemostatic paste shape 50 having an inside portion 52 comprising gelatin as first material 28 and surrounded by surface layer 54 comprising gelatin/thrombin mixture as second material 38.

Preferably, flow of first material 28 second material 38 is a laminar flow whereby materials advance side by side substantially without mixing.

Figure 10:
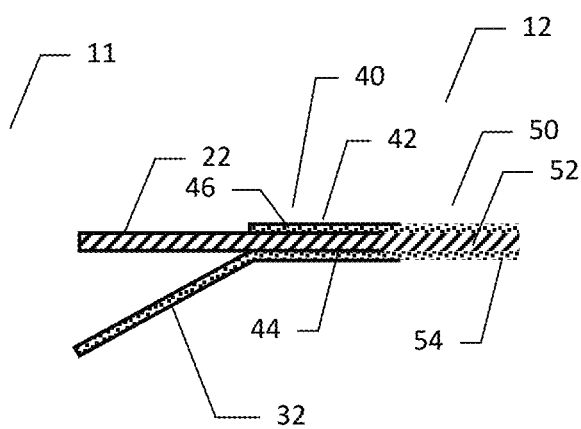
FIG. 10 shows a schematic cross-sectional view of an embodiment of the present invention.

Coaxial expression tip 40 can have tube 44 and tube 42 open and terminating at distal end 12 at the same point or at the same distance from proximal end 11, as shown in FIG. 9. In an alternative embodiment, coaxial expression tip 40 can have tube 44 and tube 42 open and terminating at distal end 12 at offset positions or at different distances from proximal end 11. As shown in FIG. 10, in one embodiment, tube 44 can terminate closer to proximate end 11, compared to tube 42, with the difference being from about 0.2 mm to about 10 mm, such as 1, 2, 5, 7 mm. As shown, opening of internal tube 44 is offset from distal end 12 compared to opening of external tube 42.

Figure 11:
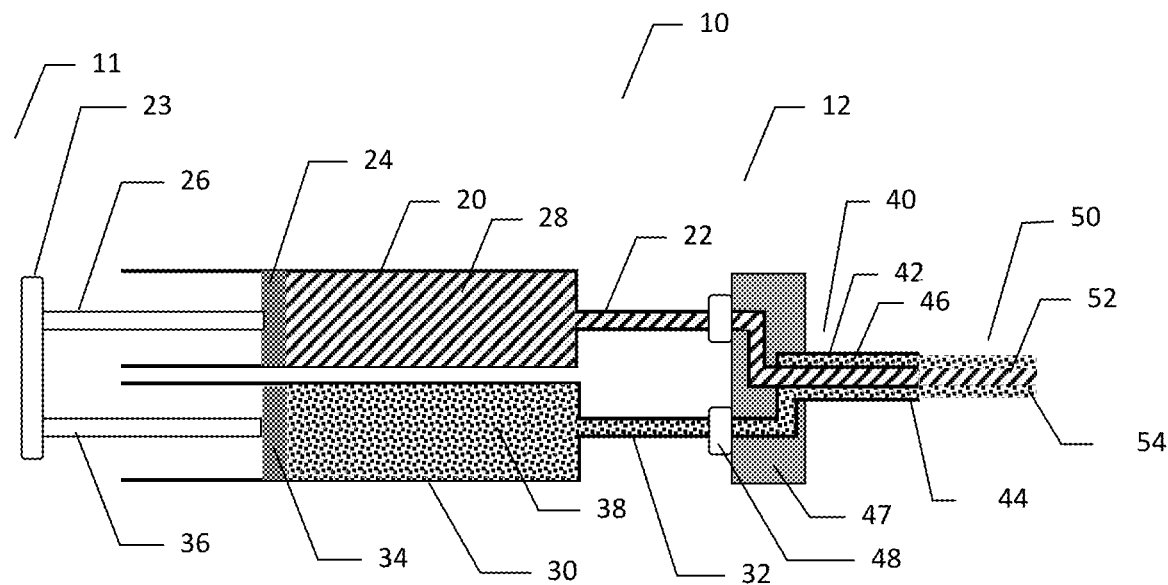
FIG. 11 shows a schematic cross-sectional view of an embodiment of the present invention.

Referring now to FIG. 11, an embodiment of the present invention is shown in a schematic cross-sectional view, like the embodiment of FIG. 9, but having a manifold 47 onto which coaxial expression tip 40 is mounted, with manifold 47 connected to expression cannulas 22 and 32 via connecting adaptors 48, which can be press-fit connectors, screw-on connectors, luer connectors, or similar.

The size or volume or diameters of first barrel hollow body 20 and second barrel hollow body 30 can be the same, or different. As shown in FIG. 11, second barrel hollow body 30 can be of the same diameter as first barrel hollow body 20.

Paste Coated by Solution or Suspension

Figure 12:
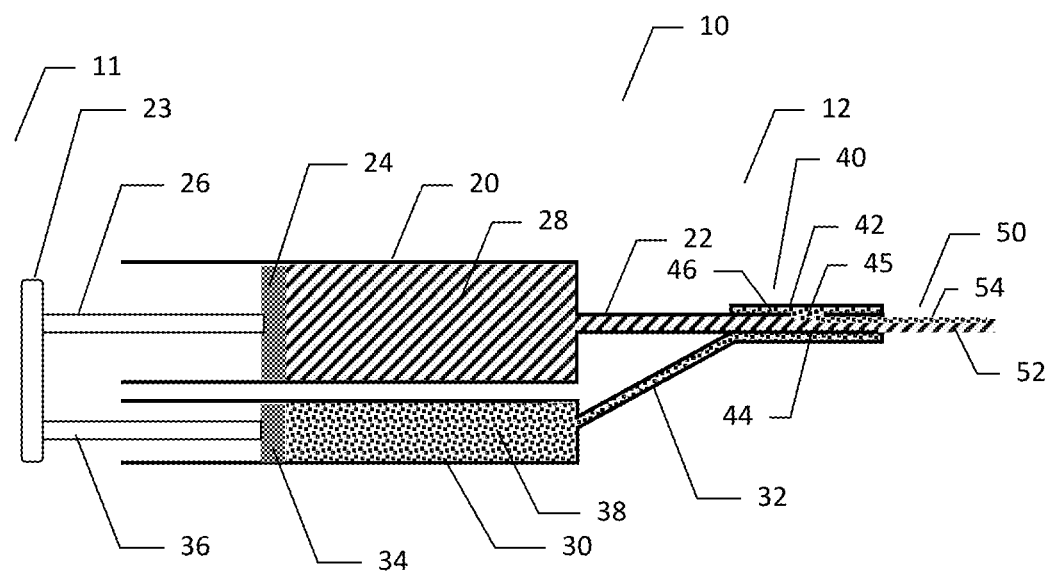
FIG. 12 shows a schematic cross-sectional view of an embodiment of the present invention.

Referring now to FIG. 12, an embodiment of the present invention shown in a schematic cross-sectional view, like the embodiments of FIGS. 9, 11, but having coaxial expression tip 40 whereby tube 42 for expression of second material 38 is not open at distal end 12, but closed. Tube 44 has at least one coating aperture 45, preferably a plurality of coating apertures 45, opening a fluid communication between tube 44 and tube 42, with aperture 45 formed in the wall of tube 44.

In operation, as materials 28 and 38 advance within tip 40, material 38 moves through gap 46 and aperture 45 and enters tube 44, then continuing alongside material 28 through tube 44 towards exiting expression tip 40 and forming at least partially coated elongated hemostatic paste shape 50 having an inside portion 52 comprising first material 28 and at least partially surrounded or partially coated by layer 54 comprising second material 38. Second material 38 can be in a form of traces on surface of first material 28.

Second material 38 comprises gelatin or collagen or similar lower viscosity flowable solution enriched by homogenously mixing with a hemostasis promoting agent, such as thrombin powder, thrombin solution, ORC, OC, or similar. More preferably, second material comprises aqueous solution of thrombin, or suspension of ORC powder.

Paste Coated by Spray of Liquid or Powder

Figure 13:
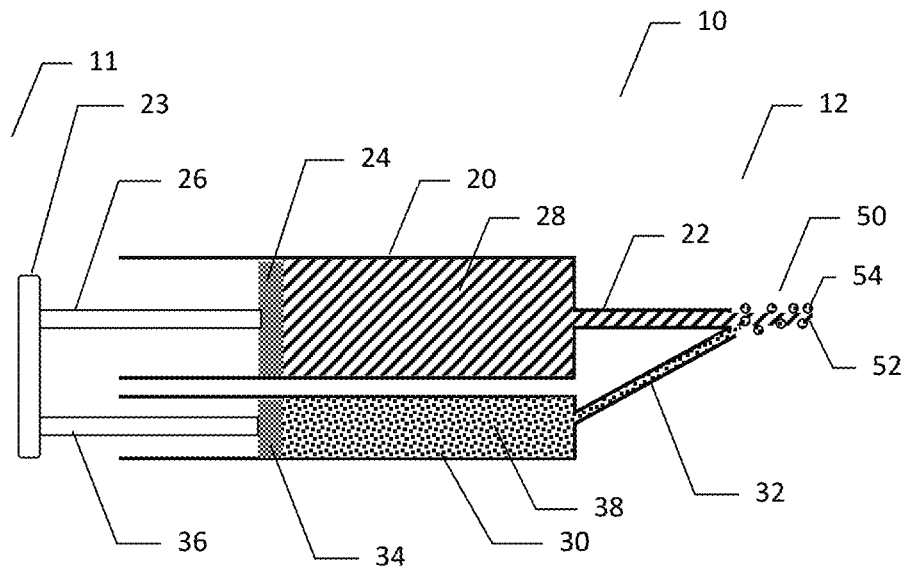
FIG. 13 shows a schematic cross-sectional view of an embodiment of the present invention.

Referring now to FIG. 13, an embodiment of the present invention shown in a schematic cross-sectional view, with no coaxial expression tip 40. In this embodiment, expression cannulas 22 and 32 terminate with closely positioned openings at distal end 12. Cannula 22 configured to express first flowable material 28, while cannula 32 configured to spray second flowable material 38 onto first material 28 as it is being expressed, forming elongated hemostatic paste shape 50 having an inside portion 52 comprising first material 28 and at least partially surrounded by surface portion 54 comprising second material 38. Second material 38 can be in a form of particles or spots on surface of first material 28.

Second material 38 comprises lower viscosity flowable solution such as thrombin solution. Alternatively, second material 38 comprises fine powder, such as thrombin powder or ORC powder, expressed from cannula 32 with the help of air flow, such as forced air or air bellows (not shown).

Paste Coated by ORC or Thrombin Powder Contained in an Enclosed Applicator

Figure 14:
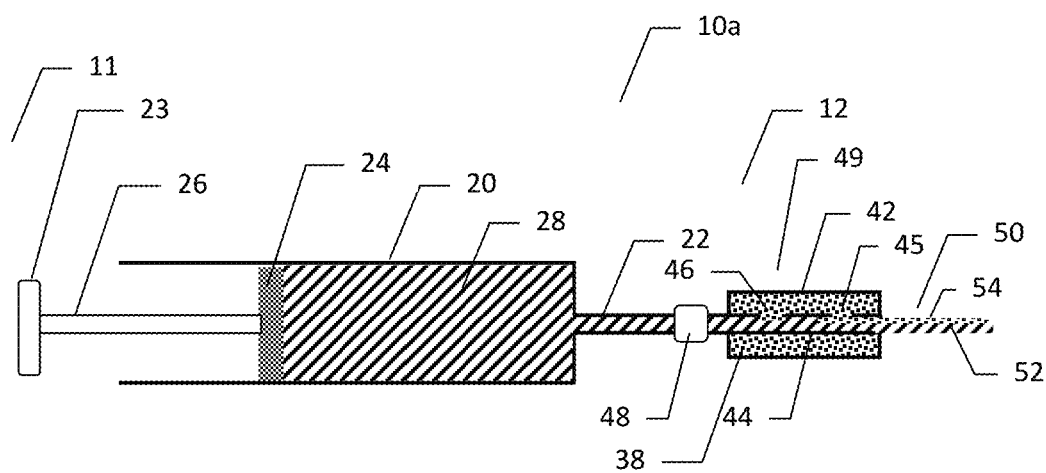
FIG. 14 shows a schematic cross-sectional view of an embodiment of the present invention.

Referring now to FIG. 14, an embodiment of the present invention shown in a schematic cross-sectional view. Delivery device 10a comprises a syringe comprising a first barrel hollow body 20 with piston 24 slidably disposed inside first body 20. Piston 24 is actuated by plunger 26 terminating in a unified handle 23 at a proximal end 11. First body 20 at a distal end 12 has expression cannula 22 through which first flowable material 28 contained inside first body 20 can be expressed onto a wound.

An applicator 49 of this embodiment is like coaxial expression tip 40 shown in FIG. 12. Tube 42 for expression of second material 38 is closed at both proximal end 11 and distal end 12. Tube 44 has at least one coating aperture 45, preferably a plurality of coating apertures 45, opening a fluid communication between tube 44 and tube 42, with aperture 45 formed in the wall of tube 44.

Applicator 49 contains fine hemostatic agent powder, such as thrombin powder, ORC powder, or similar as second material 38, and is attached to expression cannula 22 via connecting adaptor 48, which can be press-fit connector, screw-on connector, luer connector, or similar Applicator 49 comprises tube 44 for expression of first material 28, tube 44 is located inside and within tube 42. As shown, tube 42 surrounds tube 44 with a gap 46 between tubes. Second material 38 is contained within gap 46. Tube 42 is closed.

In operation, as material 28 advances through cannula 22 upon actuation of piston 24, material 28 enters applicator 49 tube 44 and entrains some of second material 38 exposed through apertures 45. Material 28 then is exiting applicator 49 through tube 44 and forming at least partially coated elongated hemostatic paste shape 50 having an inside portion 52 comprising first material 28 and at least partially surrounded or partially coated by layer 54 comprising second material 38. Second material 38 can be in a form of traces on surface of first material 28. Second material 38 can be in a form of particles or spots on surface of first material 28.

In one embodiment, tube 42 is formed of an elastic material, and is expanded or distended upon filling with second material 38 in the form of powder, thus providing compression force onto second material 38 configured to facilitate expression of material 38 through apertures 45 upon contact with first material 28 moving though tube 44.

Second material can be a powdered substance with average particle sizes ranging from about 20 to 1500 microns, more preferably 50 to 800 microns, such as 50, 100, 200, 300, 400 microns. Apertures 45 are configured to allow powdered material 38 to go through in a controlled way. In some embodiments apertures 45 have dimensions 10% to 500% larger than average particle size, such as 25, 40, 50, 75, 100%, 200%, 300% larger apertures. In some embodiments, apertures 45 are round apertures with diameter of from 100 to 500 microns.

Hemostatic Paste Extrudability and Self-Supporting Properties

According to the present invention embodiments, semi-solid and flowable paste is extrudable from devices of the present invention as an elongated form with aspect ratio of at least 3, flowable from the nozzles of the extrusion devices and maintaining elongated high aspect ratio form upon extrusion.

Upon extrusion, semi-solid paste comprises a self-supporting, shape-keeping construct, which is characterized by accepting and keeping the shape of the nozzle through which it was extruded while also being pliable and adaptable to be packed in a wound or spread over a wound. Paste is self-supporting and after expression, the paste maintains its elongated shape and form on a surface onto which the paste was expressed for at least 30 s, and not immediately changing shape without any applied force, as a regular liquid would do. On the other hand, the paste being semi-solid, the paste can be kneaded, deformed, spread over tissue, and/or packed into a wound by applying force, by hand or by using a spreading or packing tool. The paste is similar in its extrudability to the gelatin based hemostatic products such as commercially available SURGIFLO® Hemostatic Matrix.

A reference is made to the U.S. Pat. No. 7,109,163 Hemostatic compositions and devices, Pendharkar, et al., which is incorporated by reference herein in its entirety for all purposes. Pendharkar, et al. is describing hemostatic compositions with a peak expression force of no greater than 22.4 lbs. As used therein, "Peak Expression Force" is the peak force value required to extrude compositions from a pre-filled 10 cc Becton Dickinson (BD) luer syringe fitted with a 14 gauge angiocatheter tip, as described in the examples of the specification in the cited patent. Conversion of the force of the above reference into Newtons yields a force of 99.6 N.

According to the article "The Biomechanics and Optimization of the Needle-Syringe System for Injecting Triamcinolone Acetonide into Keloids", by Anthony Vo, et al., Journal of Medical Engineering, 2016, Volume 2016, Article ID 5162394, the pressure that can be generated for any syringe at a predetermined speed depends on the force exerted by the physician. An injection is conventionally performed with the thumb pushing on the plunger while the ipsilateral index and middle fingers are used to stabilize the syringe flanks. In this position, the average maximum force that can be generated is 79.8 N (males: 95.4 N, females: 64.1N). (citing Astin A. D. "Finger Force Capability: Measurement and Prediction Using Anthropometric and Myoelectric Measures", Blacksburg, Va., USA: Faculty of the Virginia Polytechnic Institute and State University; Master of Science Thesis; 1999).

Maximum isometric injection forces for two types of syringes were reported in the article "The effect of a new syringe design on the ability of rheumatoid arthritis patients to inject a biological medication", by Ali Sheikhzadeh et al., Applied ergonomics, 43 (2012) 368-375. The maximum isometric force on syringe plunger with the plunger depressed halfway was 51.99 and 77.11 N from different syringes; while with the plunger fully depressed, forces of 45.30 N and 66.51 N were observed.

However, higher expression forces can be utilized in the expression of the flowable paste of the present disclosure wherein practitioner utilizes both hands by grasping the body of the device (such as dual barrel syringe) with one hand and using another hand to depress plungers to express the semi-solid paste, or by using both thumbs pushing on the plunger. At least a double of the force can be thus developed and the present semi-solid paste should be expressible at forces at least double of the above referenced force of 79.8 N i.e. at forces up to about 159.6 N or about 160 N. Further, with power amplified or powered expression systems, such as gear-assisted, spring assisted, or motorized systems, even higher expression forces can be developed. However, the preferred way to express the paste is manual, by hand-operating an expression plunger.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A delivery device for forming and expressing a hemostatic paste material comprising:
   a) a first syringe containing a carrier material;
   b) a second syringe containing at least a supplemental hemostatic agent;

wherein said first and second syringes are joined in an integrated unit and connected to a coaxial expression tip configured for simultaneous expression of the carrier material and the supplemental hemostatic agent which both configured to exit the coaxial expression tip jointly as an elongated rod-like or noodle-like shape, with the supplemental hemostatic agent attaching onto an outside of the carrier material;

wherein the coaxial expression tip comprises an external tube and an internal tube positioned within said external tube, with a gap between the external tube and the internal tube, said paste material comprising:

the carrier material and the supplemental hemostatic agent; wherein the paste material has an elongated form extending along a lengthwise axis with an aspect ratio of at least 3, the paste material is self-supporting and syringe extrudable, and the supplemental hemostatic agent has a non-homogenous distribution profile across a cross-section taken across the lengthwise axis, wherein the external tube is closed at a distal end of said coaxial expression tip and the internal tube is open at the distal end of said coaxial expression tip, the internal tube is in fluid communication with the gap through at least one opening in a wall of the internal tube, the first syringe is connected to said internal tube at a proximal end of said coaxial expression tip and expresses the carrier material through said internal tube and the second syringe is connected to said external tube at the proximal end of said coaxial expression tip and expresses the supplemental hemostatic agent through said gap.

2. A delivery device for forming and expressing a hemostatic paste material comprising:
   a) a first syringe containing a carrier material; and
   b) a coaxial applicator tip;

wherein said coaxial applicator tip has an external tube and an internal tube positioned within said external tube, with a gap between the external tube and the internal tube; the first syringe is connected to said internal tube at a proximal end of said coaxial applicator tip and expresses the carrier material through said internal tube, a supplemental hemostatic agent is contained within said gap, the internal tube is open at a distal end of said coaxial applicator tip and the external tube is closed at the distal end of said coaxial expression tip and at the proximal end of said coaxial applicator tip, and the internal tube is in fluid communication with the gap through at least one opening in a wall of the internal tube, said paste material comprising:

the carrier material and the supplemental hemostatic agent; wherein the paste material has an elongated form extending along a lengthwise axis with an aspect ratio of at least 3, the paste material is self-supporting and syringe extrudable, and the supplemental hemostatic agent has a non-homogenous distribution profile across a cross-section taken across the lengthwise axis.

3. The device of claim 2, wherein said external tube is formed of an elastic material and the supplemental hemostatic agent is compressed by the external tube.

* * * * *